United States Patent [19]

Balasubramanian

[11] Patent Number: 5,824,322
[45] Date of Patent: Oct. 20, 1998

[54] COMPOSITIONS AND METHODS FOR GROWTH PROMOTION

[75] Inventor: Mannarsamy Balasubramanian, Roswell, Ga.

[73] Assignee: CytRx Corporation, Norcross, Ga.

[21] Appl. No.: 700,074

[22] Filed: Aug. 20, 1996

Related U.S. Application Data

[60] Provisional application No. 60/002,667 Aug. 21, 1995.
[51] Int. Cl.$^6$ .......................... A61K 45/00; A61K 47/32; A01N 31/14
[52] U.S. Cl. .................................... 424/280.1; 424/278.1; 424/283.1; 424/279.1; 568/624; 514/723; 514/772.3
[58] Field of Search .............................. 424/280.1, 278.1, 424/283.1, 279.1; 568/624; 514/723, 772.3

[56] References Cited

U.S. PATENT DOCUMENTS

| | | | |
|---|---|---|---|
| 2,674,619 | 4/1954 | Lundsted | 530/383 |
| 2,861,887 | 11/1958 | Colby et al. | 530/383 |
| 2,979,528 | 4/1961 | Lundsted | 530/383 |
| 3,740,421 | 6/1973 | Schmolka | 530/383 |
| 3,932,659 | 1/1976 | Green et al. | 514/668 |
| 4,073,886 | 2/1978 | Kehm | 530/383 |
| 4,309,413 | 1/1982 | Fields et al. | 424/78.21 |
| 4,323,467 | 4/1982 | Fu | 510/112 |
| 4,388,441 | 6/1983 | Katz | 525/54.1 |
| 4,407,790 | 10/1983 | Oakes et al. | 514/723 |
| 4,557,898 | 12/1985 | Green et al. | 424/616 |
| 5,114,708 | 5/1992 | Hunter | 514/716 |
| 5,183,687 | 2/1993 | Hunter et al. | 424/78.34 |
| 5,234,683 | 8/1993 | Hunter et al. | 424/78.31 |
| 5,358,653 | 10/1994 | Gladfelter et al. | 252/90 |
| 5,466,445 | 11/1995 | Hunter | 424/78.31 |
| 5,494,660 | 2/1996 | Hunter et al. | 424/78.31 |
| 5,554,372 | 9/1996 | Hunter | 424/280.1 |

FOREIGN PATENT DOCUMENTS

WO/86/07539  12/1986  WIPO.

OTHER PUBLICATIONS

Brem et al., "Interstitial Chemotherapy with Drug Polymer Implants For The Treatment of Recurrent Gliomas," *J. Neurosurg.*, vol. 74, pp. 441–446 (1991).

Schmolka, "A Review of Block Polymer Surfactants," *Journal of American Oil Chemists Society*, vol. 54, No. 3, pp. 110–116 (1977).

Hunter and Bennett, "The Adjuvant Activity of Nonionic Block Polymer Surfactants. II. Antibody Formation and Inflammation Related to the Structure of Triblock and Octablock Copolymers," *Journal of Immunology*, vol. 133, pp. 3167–3175 (1984).

Hunter et al., "The Adjuvant Activity of Nonionic Block Polymer Surfactants. I. The Role of Hydrophile–Lipophile Balance," *Journal of Immunology*, vol. 127, pp. 1244–1250 (1981).

Atkinson et al. "Induction of Suppressor Cells by Reverse Block Copolymers," Abstract #7596, *Federation Proceedings*, vol. 44, p. 1710 (Mar. 1985).

Kendall, "Have We Underestimated the Importance of the Thymus in Man?" *Experentia*, vol. 40, pp. 1181–1185 (1982).

Hunter et al. "The Adjuvant Activity of Nonionic Block Polymer Surfactants. III. Characterization of Selected Biologically Active Surfaces," *Scand. Journal of Immunology*, vol. 23, pp. 287–300 (1986).

Hunter et al., "Structural Basis of the Activity of the Surface–Active Adjuvants," *Advances in Carriers & Adjuvant for Veterinary Biologics*, The Iowa State University Press, Chapter 6, pp. 61–70 (1986).

Ceresa, ed., "The Applications of Block Polyol Surfactants," *Block and Graft Copolymerization*, vol. 2, pp. 174–272 (1976).

Rodeheaver, G.T., "Pluronic F–68: A Promising New Skin Wound Cleanser," *Ann. Emerg. Med.*, vol. 9, pp. 572–576 (1980).

Koff et al., "Human Monocytes Activated by Immunomodulators in Liposomes Lyse Herpesvirus–Infected but Not Normal Cells," *Abstract Science*, vol. 224, pp. 1007–1009 (Jun. 1, 1984).

Koff et al., "Protection of Mice Against Fatal Herpes Simplex Type 2 Infection by Liposomes Containing Muramyl Tripeptide," Abstract, *Science*, vol. 228, 495–497 (Apr. 26, 1985.).

Weksler, M.E., MD., "The Thymus Gland and Aging," *Annals of Internal Medicine*, vol. 98, No. 1, pp. 105–107 (Jan. 1983).

Rivera et al., "Is There Danger In Our Food?" Transcript from ABC News 20/20 Program, Jun. 20, 1985 pp. 7–13.

Amiji, M. et al. "Prevention of Protein Adsorption and Platelet Adhesion on Surfaces by PEO/PPO/PEO Triblock Copolymers," *Biomaterials*, vol. 13, No. 10, pp. 682–692 (1992).

*Primary Examiner*—Ponnathapura Achutamurthy
*Assistant Examiner*—P. Ponnaluri
*Attorney, Agent, or Firm*—Jones & Askew, LLP

[57] ABSTRACT

The present invention includes compositions and methods using biologically active nonionic reverse block copolymers. The reverse copolymers have an inner core of polyoxypropylene (POP) that is flanked on either end by polyoxyethylene (POE). The reverse block copolymers have the following formula:

$$HO(C_3H_6O)_b(C_2H_4O)_a(C_3H_6O)_bH$$

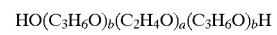

POP    POE    POP wherein "b" represents a number such that the molecular weight of the hydrophobe $(C_3H_6O)_b$ is between approximately 2,000 and 10,000, and "a" represents a number such that the percentage of hydrophile $(C_2H_4O)_a$ is between approximately 5% and 30%. The reverse block copolymers stimulate the immune response, can suppress immune responses such as those in autoimmune diseases, promote the growth of animals, and stimulate hormone production.

8 Claims, No Drawings

COMPOSITIONS AND METHODS FOR GROWTH PROMOTION

This application claims the benefit of U.S. provisional application Ser. No. 60/002,667, filed Aug. 21, 1995.

TECHNICAL FILED

The present invention relates to compounds with a variety of biological activities and more particularly, to a series of block copolymers that have a wide variety of effects on living cells and organisms.

BACKGROUND OF THE INVENTION

The present invention is a class of compounds that has a wide variety of profound biological effects. Background material concerning several of these biological activities is discussed hereinbelow.

IMMUNE STIMULATING COMPOUNDS

The immune system is a highly complex system of cells and tissues that requires the cooperation of a large number of different cell types. The systems of the body that make up the immune system network are variously categorized as belonging to the hematopoietic system, the reticuloendothelial or phagocytic system and the lymphoid system.

The hematopoietic system is located in the bone marrow and is responsible for supplying the various precursor and accessory cells of the immune systems. The reticuloendothelial system is made up of the phagocytic cells that are responsible for destroying or neutralizing foreign material that may enter the body. The lymphoid system is made up of lymphocytes, and is responsible for the overall regulation of the immune system and for the production of antibodies.

The tissues of the lymphoid system are generally classified as the central tissues and the peripheral tissues. Two central lymphoid tissues of mammals are bone marrow and thymus. In addition, fowl have a third central lymphoid organ, the bursa of Fabricius, which is critical to the development of the immunoglobulin-producing cells. It is thought that the mammals have a bursal equivalent associated with the intestinal tract. Lymph nodes, spleen, tonsils, intestinal lymphoid tissue (Peyer's patches) and other collections of lymphocytes constitute the peripheral lymphoid tissues.

In mammals, the bone marrow, if considered as a single tissue, is the largest tissue of the body. In the average human adult the total weight of the bone marrow is about 3 kg. Marrow fills the central core of nearly all bones. Bone marrow has three types of tissue: vascular tissue, adipose tissue and the tissue directed to hematopoiesis or blood cell formation. The vascular tissue is the circulatory system that supplies nutrients and removes wastes from the actively growing cells. The hematopoietic tissue is responsible for the formation of erythrocytes, platelets, granulocytes and monocytes, and lymphocyte precursors. Adipose tissue consists of fat cells which contribute little to the function of the bone marrow.

The other central lymphoid tissue is the thymus—a bilobed organ situated in the anterior thoracic cage over the heart. In other species, the thymus may be distributed along the neck and thorax in several lobules.

Embryologically, the thymus emerges from the third and fourth branchial pouches. The human thymus is a fully developed organ at birth and weighs 15 to 20 grams. By puberty it weighs 40 grams, after which it atrophies or involutes becoming less significant structurally and functionally. Atrophy of the thymus with age is a characteristic of all species which is associated with aging and the cessation of growth. The incidence of age related diseases increases as the thymus shrinks and thymus-dependent immunity decreases. This age-associated decrease in thymic weight, called involution, is accompanied by changes in the thymic structure and a general decline in thymic function. Transient involution of the thymus may also occur as a consequence of a stress or infection. Thymic involution may be controlled hormonally; castration slows involution while injection of corticosteroid hormones accelerates involution. Numerous studies have demonstrated that the thymic involution associated with increasing age parallels a reduction of T-lymphocyte-mediated immunity and increased incidence of diseases associated with aging. Many diseases and treatments can accelerate involution of the thymus; virtually none are known to enhance growth of the thymus or reverse involution.

Anatomically, the thymus is a pouch of epithelial cells filled with lymphocytes, nourished and drained by the vascular and lymphatic systems and innervated by the autonomic nerves. The epithelial cells and other structural cells divide the thymus into a complex assembly of continuous lobes, each of which is heavily laden with lymphocytes. The epithelial cells produce hormones and regulate some of the activities of the lymphocytes. The lymphocyte population is greatest in the cortex or outer portion of each lobule. The inner section, the medulla, has more epithelial cells and fewer lymphocytes but the lymphocytes are more mature.

Lymphocytes can generally be classified as either T-lymphocytes or as B-lymphocytes. B-lymphocytes are responsible for the production of antibodies (immunoglobulin) in response to a challenge by a particular antigen. T-lymphocytes are responsible for the general regulation of the immune system and are also the principal mediators in cell-mediated immune responses. They also influence the proliferation of bone marrow cells and are probably involved in the growth and differentiation of other organs as well.

All lymphocytes are ultimately derived from stem cells in bone marrow. These lymphocyte precursors are dispersed into the blood where they course through many organs. However, critical events take place in the thymus and bursa of Fabricius (or its mammalian equivalent) that imprint the lymphocytes with special functions and that regulate the development into either T or B-lymphocytes.

Life-span studies of lymphocytes of most mammalian species divide lymphocytes into two fractions—those with a short span (mostly large lymphocytes) of 5 to 7 days and the small lymphocytes with a life span measured in months or even years. The former are usually B-lymphocytes and the latter are usually T-lymphocytes.

B-lymphocytes respond to immunologic phenomena very differently from a T-lymphocyte in practically every instance. T-lymphocytes are formed in the thymus from lymphoblasts that left the bone marrow. This maturation is expressed morphologically as a reduction in cell size to about 7 $\mu$m in diameter. The thymic cortex is rich in lymphocytes of all sizes. These thymocytes are not morphologically distinguishable from lymphocytes in other tissues, but they are immature and antigenically identifiable by the presence of several cell surface antigens including the $\phi$, or T antigen, a distinctive surface marker antigen that separates the T-lymphocyte from the B-lymphocyte.

Enumeration of lymphocytes indicate that 65% to 85% of all lymphocytes in the blood are of the T type. Lymphocytes of the thoracic duct fluid are nearly 90% to 95% of the T variety and those in the Peyer's patches or the gut are 50% to 65% T-lymphocytes. The T-lymphocyte population of lymph nodes, particularly in the deep cortical region, is high, but is low in the tonsil and the appendix.

When the T-lymphocyte contacts a recognizable antigen in the appropriate context, it passes through a phase of growth and cell division known as lymphocyte transformation to produce a large population of its own kind. The antigen must first be "processed" by macrophages and then presented to T-lymphocytes.

T-lymphocytes are actually divided into several subsets and the role they play in the immune system is complex. The T-lymphocyte is responsible for the phenomenon known as the cell-mediated immune response. In a cell-mediated immune response, the T-lymphocytes that recognize a cell-bound antigen begin producing and secreting a wide variety of proteins that affect the activity of other types of cells in the immune system. These proteins include lymphokines and monokines that attract, activate and hold phagocytes at the site of the antigen and interferons that provide protection against virus infection.

The T-lymphocyte is also an important regulator of B-lymphocyte function. The antigen-exposed T-lymphocyte may have either of two direct and opposite effects on B-lymphocytes depending on the subclass of T-lymphocyte. The major subclasses are the helper cell and the suppressor cell. Helper T-lymphocytes are necessary for a complete B cell response to T-lymphocyte-dependent antigens. T-lymphocyte dependent antigens tend to be the more complex antigens such as bacterial proteins, virus proteins and other large complex proteins in general.

Unlike helper T-lymphocytes, suppressor T-lymphocytes block the development of effector B and T lymphocytes. Specific suppressor T-lymphocytes have now been demonstrated to play a large role in tolerance to many proteins, both in antibody and cell-mediated immune responses. In addition, genetic unresponsiveness to some antigens is due to the greater stimulation of suppressor T-lymphocytes than of helper T-lymphocytes by these antigens.

Thus, in the normal, healthy animal, the thymus is normally active only during the early years of life. During these early years of thymic activity, the thymus supplies the animal with the T-lymphocytes which will serve the animal for the rest of its life. In certain diseases, such as rheumatoid arthritis, the thymus may regain some activity during adult life. This demonstrates that the adult thymus retains capacity to function and that involution is not necessarily permanent. At least partial function might be restored if the appropriate agents were available.

Acquired T-lymphocyte deficiency diseases of adults are characterized by a depletion of circulating T-lymphocytes. The symptoms expressed in these diseases include an inability to mount a cell-mediated immune response to an antigen challenge. An example of an acquired T-lymphocyte deficiency disease is acquired immune deficiency syndrome, or AIDS.

AIDS is a disease caused by the human T-lymphocyte lymphotrophic virus (LAV or HTLV-III). The virus specifically attacks CD4+ helper lymphocytes, a subgroup of T-lymphocytes that plays a major role in defending the body against infectious diseases. Depletion of this subset of lymphocytes is manifested by an increased incidence of opportunistic infections like *Pneumocystis carinii M. tuberculosis, toxoplasma gondii*, and certain cancers. More specifically, the virus enters the T-lymphocyte and incorporates viral encoded DNA into the DNA of the host T-lymphocyte. As long as the infected T-lymphocyte remains inactivated, the virus will remain quiescent in the DNA of the host cell. Although not proven, it is thought that the infected T-lymphocytes are activated by stimuli such as a specific antigen, the viral DNA in the host DNA is expressed and produces new viral particles. The host T-lymphocyte is then killed and lysed, releasing new viral particles that can invade and kill other T-lymphocytes. The loss of $CD^4+$ lymphocytes is profound and occurs even faster than can be accounted for by direct viral killing of the cells. This has led some investigators to postulate that the infection somehow shuts off the production of CD4+ lymphocytes. In any case, the thymus in the normal adult is no longer functioning and the killed T-lymphocytes cannot be replaced, leaving the patient vulnerable to subsequent infections. Especially striking are recent studies of the thymuses of deceased AIDS patients ranging in age from 10 months to 42 years. AIDS victims have profound thymic involution— much more extensive than in age-matched patients who died of other causes.

The cure of a person with AIDS will probably require one agent to eliminate the virus and other agents to cause the body to regenerate the T cell population that have been killed by the virus. The first step is to eliminate the AIDS virus from the patient. This will have to be supported by other therapies to induce restoration of immune function. Studies to date with macrophage activating agents, interferon inducers and lymphokines have been disappointing, possibly because their targets, T-lymphocytes, do not exist in sufficient numbers. Interleukin 2 restores the function of one subset of non T-cells (natural killer cells) but has no effect on a host of other serious defects. More drastic measures can be performed. One potential method of restoring the immune system is by transplanting bone marrow from healthy donors. However, this is a dangerous procedure. It may produce lethal graft versus host disease unless the patient's donor is an identical haplotypic match.

Another area where there is a need to re-establish not only the immune system, but also the hematopoietic system, is in total body irradiation for treatment of leukemia. When a patient undergoes high dose total body irradiation, the entire immune system is destroyed. The usual treatment after the irradiation is to perform a bone marrow transplant with marrow from a close relative. If the transplant is successful, the new marrow will produce new cells, thereby restoring both red blood cells and white blood cells to the body. However, this is a dangerous treatment that is successful in only a fraction of the cases. Localized radiation of tumors and several types of chemotherapy also produce suppression of T-cell mediated immunity.

What is needed is a safe and effective method of re-establishing T-lymphocytes and T-lymphocyte function. One method of re-establishing T-lymphocyte function is by treating existing T-lymphocytes so that they resume their normal immune functions. Agents that have been shown to be effective in certain situations in stimulating T-lymphocytes include macrophage activating factors, interferon inducing agents, lymphokines, monokines and cytokines. However, in a disease such as AIDS or in the case of irradiation in which the T-lymphocyte population has been destroyed, this type of treatment is not effective because the number of T-lymphocytes is severely depleted. In these cases, an effective method of causing the thymus to produce new T-lymphocytes would be the treatment of choice. However, to date, there is no effective treatment that will cause the thymus to reverse the process of involution and produce new T-lymphocytes.

AUTOIMMUNE DISEASES

Autoimmune diseases are characterized by the development of an immune reaction to self components. Normally, tissues of the body are protected from attack by the immune system; in autoimmune diseases there is a breakdown of the self-protection mechanisms and an immune response directed to various components of the body ensues. Autoimmune diseases are for the most part chronic and require lifelong therapy. The number of recognized autoimmune diseases is large and consists of a continuum ranging from diseases affecting a single organ system to those affecting several organ systems. With increased understanding of the molecular basis of disease processes, many more diseases will likely be found to have an autoimmune component. Specific examples of autoimmune diseases are presented below.

| Organ Specific | Hashimoto's thyroiditis |
| --- | --- |
| | Graves' disease |
| | Addison's disease |
| | Juvenile diabetes (Type I) |
| | Myasthenia gravis |
| | Pemphigus vulgaris |
| | Sympathetic ophthalmia |
| | Multiple sclerosis |
| | Autoimmune hemolytic anemia |
| | Active chronic hepatitis |
| | Rheumatoid arthritis |
| Non-organ specific | Systemic lupus erythematosus |

Systemic lupus erythematosus (SLE) is an inflammatory, multisystem disease characterized clinically as a relapsing disease of acute or insidious onset that may involve any organ in the body. Clinically, symptoms are due to disease affecting the skin, kidneys, serosal membranes, joints, hair folicles and heart. Anatomically, all sites have in common vascular lesions with fibrinoid deposits and immunologically, the disease involves antibodies of autoimmune origin, especially antinuclear antibodies (ANA). The ANA are directed against both DNA and RNA. Autoantibody development appears to be multifactorial in origin, involving genetic, hormonal, immunologic and environmental factors.

The morphologic changes seen in organs result from the formation of circulating immune complexes and their deposition in a variety of tissues. Although many organs can be affected, some are affected more than others. Lesions of joints, the kidneys, heart, and serous membranes are responsible for most of the clinical signs. The course of SLE is extremely variable and unpredictable. An acute onset with progressive downhill course to death within months can occur. The usual course however, is characterized by flare-ups and remissions spanning a period of years or even decades. It usually arises in the second or third decades of life, but may become manifest at any age.

Acute attacks are usually treated by adrenocortical steroids or immunosuppressive drugs. These drugs often control the acute manifestations. With cessation of therapy the disease usually reexacerbates. The prognosis has improved in the recent past; approximately 70 to 80% of patients are alive 5 years after the onset of illness and 60% at 10 years. Lifelong therapy is required to control the disease.

At one time SLE was considered to be a fairly rare disease. Better methods of diagnosis and increased awareness that it may be mild and insidious have made it evident that its prevalence may be as high as 1 case per 10,000 population. There is a strong female preponderance—about 10 to 1.

Rheumatoid arthritis is a systemic, chronic, inflammatory disease that principally affects the joints and sometimes many other organs and tissues throughout the body. The disease is characterized by a nonsuppurative proliferative synovitis, which in time leads to the destruction of articular cartilage and progressive disabling arthritis. The disease is caused by persistent and self-perpetuating inflammation resulting from immunologic processes taking place in the joints. As is the case with most autoimmune diseases, the trigger that initiates the immune reaction remains unidentified. Both humoral and cell-mediated immune responses are involved in the pathogenesis of rheumatoid arthritis. The majority of patients have elevated levels of serum immunoglobulins and essentially all patients have an antibody-based rheumatoid factor (RF) directed against a component of another antibody class.

The key event in the pathogenesis of the arthritis is the formation of antibodies directed against other self antibodies. Why these antibodies are formed is unknown at present. It has been suggested that the process is initiated by the formation of antibodies or immunoglobulins against an unknown antigen, possibly an infectious agent. When the antibodies combine with the antigen, conformational changes occur in a portion of the antibody molecule creating new antigenic determinants. The appearance of new determinants evokes an antibody response against the antibody molecule and results in the formation of anti-immunoglobulin antibodies or rheumatoid factor. T cells may also be involved in the pathogenesis of rheumatoid arthritis by way of providing helping cytokines that exacerbate the disorder. A large number of T cells are found in the synovial membrane, outnumbering B cells and plasma cells. Additionally, procedures to decrease the population of T cells (such as draining the thoracic duct), result in remission of symptoms.

The most destructive effects of rheumatoid arthritis are seen in the joints. Classically, it produces symmetric arthritis, which principally affects the small joints of the hands and feet, ankles, knees, wrists, elbows, shoulders, temporo-mandibular joints and sometimes the joints of the vertebral column. The clinical course is highly variable. After approximately 10 years, the disease in about 50% of the patients becomes stabilized or may even regress. Most of the remainder pursue a chronic, remitting, relapsing course. After 10 to 15 years, approximately 10% of patients become permanently and severely crippled. The disease usually has its onset in young adults but may begin at any age and is 3 to 5 times more common in women than in men.

Rheumatoid arthritis is a very common disease and is variously reported (depending on diagnostic criteria) to affect 0.5 to 3.8% of women and 0.1 to 1.3% of men in the United States.

Multiple sclerosis is another disease that is thought to be caused by autoimmune mechanisms. The cause of multiple sclerosis is unknown but seems to be multifactorial. Susceptibility or resistance may be genetically determined; something in the environment interacts with the human host at the proper age to cause biochemical and structural lesions in the central nervous system. The systemic immune response and the response of the central nervous system become involved. Although the cause and pathogenesis of multiple sclerosis are unknown, it is widely believed that immune abnormalities are somehow related to the disease. Three possible mechanisms have been postulated: infection, autoimmunity, and a combination of the two. Suppression or modulation of the immune responses may be the key.

The graphic distribution of multiple sclerosis indicates that the disease may be acquired from an environmental factor. Approximately 200 studies of the geographic distribution of multiple sclerosis have been conducted and have shown that regions of high prevalence (30 to 80 cases per 100,000 population) in northern Europe between 65 and 45 degrees north latitude and in the northern United States and southern Canada, as well as in southern Australia and New Zealand. In contrast, regions of low risk, including most of Asia and Africa, have a prevalence of 5 or fewer cases per 100,000.

Myasthenia gravis is an autoimmune disorder caused by antibodies directed against the acetylcholine receptor of skeletal muscle. Present information indicates at least three mechanisms whereby acetylcholine receptor antibody may interfere with neuromuscular transmission and thus induce myasthenia gravis. Acetylcholine receptor antibody may interfere (directly or indirectly) with acetylcholine receptor function. In both experimental allergic myasthenia gravis and human myasthenia gravis, the extent of acetylcholine receptor loss parallels the clinical severity of the disease, suggesting that acetylcholine receptor antibody-induced acceleration of acetylcholine receptor degradation is important in the development of myasthenia gravis. Complement-mediated destruction of the postsynaptic region is the third possible cause. Other disorders, especially those presumed to be autoimmune in origin, can occur in association with myasthenia gravis. Thyroid disease, rheumatoid arthritis, systemic lupus erythematosus, and pernicious anemia all occur more commonly with myasthenia gravis than would be expected by chance. The prevalence of myasthenia gravis in the United States is one per 20,000.

The foundation of therapy for autoimmune diseases is treatment with immunosuppressive agents. The basis for this therapy is attenuation of the self-directed immune response with the primary aim being to control symptoms of the particular disease. The drugs utilized to achieve this aim are far from satisfactory, in that adverse side effects are numerous and control of the disease is many times difficult to achieve. The problem is compounded by the chronicity of the disease with effective therapy becoming more difficult with time. An indication of the severity of particular diseases is seen in the willingness to accept greater risks associated with therapy as the disease progresses. Currently available therapy is distinctly non-selective in nature, having broad effects on both the humoral and cell-mediated arms of the immune system. This lack of specificity can limit the effectiveness of certain therapeutic regimens. The main groups of chemical immunosuppressives are alkylating agents, antimetabolites, corticosteroids, and antibiotics. Each will be discussed briefly.

The corticosteroids, also called adrenocorticosteroids, are fat-like compounds produced by the outer layer, or cortex, of the adrenal gland. The adrenal cortex is an organ of homeostasis influencing the function of most systems in the body. It is responsible for adaptation of the body to a changing environment. Therapeutic use of the corticosteroids for autoimmune disease is based on their two primary effects on the immune system: anti-inflammatory action and destruction of susceptible lymphocytes. They also effect a redistribution of lymphocytes from peripheral blood back to the bone marrow. The use of corticosteroids is not without adverse side effects however, particularly during the course of lifelong treatment which is required for many of the autoimmune diseases. Major side effects of steroids are:

1. Cushing syndrome
2. Muscle atrophy
3. Osteoporosis
4. Steroid induced diabetes
5. Atrophy of the adrenal glands
6. Interference with growth
7. Susceptibility to infections
8. Aseptic bone necrosis
9. Cataract development
10. Gastric ulcer
11. Steroid psychosis
12. Skin alterations
13. Nervous state accompanied by insomnia Attempts to minimize side effects incorporate alternate day or less frequent dosage regimens.

An effective immunosuppressive agent is the antibiotic cyclosporin A. The antibiotic has greatest activity against T cells and has little to no effect on B cells. The drug is being evaluated for the treatment of autoimmune diseases for which it shows some promise. Side effects include hair growth, mild water retention, renal toxicity, and, in older patients, nervous system disorder symptoms.

Other drugs are used alone or in combination with those listed above and include gold salts and antimalarials, such as chloroquine. Another class of drugs, the nonsteroidal anti-inflammatory drugs, are used extensively in arthritis. These drugs provide analgesia at low doses and are anti-inflammatory after repeated administration of high doses. Nonsteroidal anti-inflammatory drugs all act rapidly and their clinical effects decline promptly after cessation of therapy. They do not prevent the progression of rheumatoid arthritis and do not induce remission. Immunostimulants, such as levamisol, have also been used in many autoimmune diseases but side effects have generally limited their use.

GROWTH PROMOTING COMPOUNDS

With an ever-increasing world demand for food, there is constant pressure to increase the rate of production of food. In the early 1950s, researchers unexpectedly discovered that an antibiotic ingredient in chicken mash was a "growth factor." The finding drastically changed the nation's livestock and poultry production and was an economic boon for pharmaceutical companies. Food animals are now raised under highly controlled conditions and receive specialized feed with a variety of growth promoting additives.

Routine antibiotic administration to animals has become almost universal since the discovery that the addition of small amounts of antibiotics such as penicillin, tetracycline and sulfamethazine, to animal feed increases the growth of pigs and cattle. In 1979, about 70% of the beef cattle and veal, 90% of the swine, and virtually 100% of broilers reared in the United States consumed antibiotics as part of their daily feed. This use, accounting for nearly 40% of antibiotics sold in the United States, is estimated to save consumers $3.5 billion a year in food costs.

Animals raised under modern conditions optimized for growth promotion receive rations containing high proportions of protein, usually in the form of soybean or cottonseed meal, and high percentages of grains such as corn or milo, a type of sorghum. Feed additives which have been used include such hormones as diethylstilbestrol, or DES which also increases the rate of weight gain, and tranquilizers that prevent the effects of the stress brought on by confinement conditions from causing disease or weight loss.

Cattle ordinarily require 10 pounds of feed to produce one pound of weight gain. Under optimal growth promoting conditions and with enriched feed they gain one pound with only 6 pounds of feed.

Modern farming has greatly reduced the labor required to raise farm animals. In broiler chicken raising, where intensive methods have had the most dramatic effect, it took 16 hours of labor to raise a flock of 100 broilers in 1945; in 1970 that figure was reduced to 1.4 labor hours, in part because of the use of automated confinement facilities and associated advances in breeding and nutrition.

Although hormones and antibiotics have greatly increased the rate of growth of food animals, the use of such additives has not been without problems. One of the hormones that was commonly used as a growth stimulant, diethylstilbestrol, has been shown to be a carcinogen and has been banned from further use in most countries.

When antibiotics are mixed in animal feed, the compounds are spread throughout the environment exposing external microorganisms to the antibiotics. The constant exposure of the microorganisms to antibiotics puts biological pressure on the microorganisms to develop resistance to the antibiotics. This can result in a microorganism that is resistant to antibiotics.

An antibiotic-resistant microorganism is potentially a serious pathogen because it is difficult to control. If the organism causes an infection in an animal or in a human, the infection may not be controlled with conventional antibiotics. If the infection is serious, there may not be time to determine which antibiotics are effective against the infecting bacteria. The problem has been especially serious when antibiotic-resistant organisms in meat are consumed by people who themselves take antibiotics for treatment of disease. Antibiotics inhibit many of the normal microorganisms in the respiratory and gastrointestinal tracts. This allows the resistant ones to proliferate rapidly and produce more serious disease. The combination of antibiotic-resistant organisms from food and ineffective antibiotic treatment of people has resulted in most of the deaths due to Salmonella food poisoning reported in the United States in the past several years.

As a result of the increasing appearance of antibiotic-resistant bacteria in feed lots and several serious epidemics caused by antibiotic resistant bacteria, there is increasing governmental pressure to limit the use of antibiotics in animal feed. Consequently, there is an immediate and increasing need for new, safe and effective growth stimulators of farm animals.

REDUCING ENTERIC MICROORGANISMS

While many enteric microorganisms are beneficial to their host and reside in the host's gut without adverse consequence, many other enteric microorganisms are pathogenic and cause various and often severe disease states. For example, typhoid fever is caused by Salmonella, bacillary dysentery is caused by Shigella, and cholera is caused by Vibrio. These disease states remain a major public health threat in lesser developed countries. One approach to managing these diseases would be to treat patients, either before or after manifestation of disease symptoms, to reduce the number of microorganisms in the gut.

Additionally, the prevalence of Salmonella in animals, particularly birds, more particularly poultry such as chickens, turkeys, pheasant, quail, geese, ducks, emus, ostriches and other ratites, constitutes a constant source of expense to the farming and food industries as well as a health threat to consumers.

Further, pet fecal odor is a significant problem, particularly for house bound pets such as cats. Fecal odor is caused by certain intestinal microorganisms, and is diminished or eliminated if odor-producing microorganisms are reduced in the intestinal tract of the pet.

Consequently, there is an immediate need for compositions and methods for reducing enteric microorganisms and pathogens in humans, in farm animals, particularly Salmonella in poultry such as chickens, and in household pets.

ANTITUMOR COMPOUNDS

Malignant, or cancerous, tumors are defined by their invasion of local tissue and their ability to spread or metastasize to other parts of the body. The incidence of tumors is high; it is the second leading cause of death in both children and adults. A malignant tumor, by definition, always kills (unless treated) because of its invasive and metastatic characteristics. The tumor grows locally by encroachment into the normal tissues surrounding it. The tumor spreads to distant sites by the breaking off of malignant cells. These cells then move through the blood and lymphatic systems, attach themselves, and begin to grow as new colonies.

The factors controlling tumor growth are poorly understood. Tumors in laboratory animals may be transplanted to a second host using only a single tumor cell. This facility suggests that only one normal cell need become transformed (cancerous) for tumor growth to begin. It is thought, however, that many transformed cells die or remain latent or dormant for extended periods before successful tumor growth is established. Tumors have been experimentally induced in animals by chemical, physical, and viral agents, and by radiation and chronic irritation.

Leukemia is a term given to tumors of the blood-forming organs. The acute and chronic leukemias, together with the other types of tumors of the blood, bone marrow cells (myelomas), and lymph tissue (lymphomas), cause about 10% of all cancer deaths and about 50% of all cancer deaths in children and adults less than 30 years old. At least 4 million people now living are expected to die from these forms of cancer, assuming there are no major advancements made in the treatment of these diseases.

Conventional treatment regimens for leukemia and for other tumors include radiation, chemotherapy, or a combination of both. In addition to radiation, the following drugs, usually administered in combination therapy, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. All of the conventional anti-cancer drugs are highly toxic and tend to make patients quite ill while undergoing treatment. Vigorous therapy is based on the premise that unless every leukemic cell is destroyed, the residual cells will multiply and cause a relapse.

Most of the conventional chemotherapeutic drugs that are being used in tumor therapy do not specifically target the killing of tumor cells. Reliance is placed on the fact that, in most cancers, the cancerous cells grow faster than normal cells and will therefore utilize more of the toxic chemotherapeutic drug thereby killing the cancer cell. Administration of the conventional chemotherapeutics requires careful attention to the amount and concentration of the drug or combination of drugs so that the cancer cells will be killed but normal cells will survive. For this reason, it is difficult to kill all cancerous cells by conventional chemotherapy.

What is needed are compounds that will specifically and completely kill cancerous cells while not affecting normal cells. Ideally, the new compounds would take advantage of physical characteristics inherent only in the tumor cell. For example, a tumor cell may be more sensitive than normal cells to changes in ion concentrations within the cell. If a compound could detrimentally vary the internal ion concentrations of the tumor cells, then the compound could specifically kill the tumor cell while not adversely affecting normal cells.

IONOPHORIC COMPOUNDS

Ionophores are defined as substances capable of interacting stoichoimetrically with metal ions so as to transport the ions across a hydrophobic barrier such as a cell membrane.

It has been generally accepted that cell membranes consist of a phospholipid bilayer interspersed with globular protein molecules. The hydrophilic phosphate portions of the phospholipid are oriented at the outer edges of the membrane while the hydrophobic lipid portions face toward the center. The cell membrane is selectively permeable and will permit water, certain nutrients and essential metal ions to pass freely into the cell when needed. However, due to the double layer of nonpolar lipids in its center, the membrane is normally impermeable to highly polar molecules.

Different ionophores often have an affinity for one ion or one group of ions over another. The ions most commonly transported across cell membranes include $Na^+$, $K^+$, $Li^+$, $Rb^+$, $Cs^+$, $Ca^{+2}$, $Mg^{+2}$, $Ba^{+2}$, $Cu^{+2}$, $Mn^{+2}$, $Fe^{+2}$, $Ni^{+2}$, and $Zn^{+2}$. For example, the negatively charged fungal antibiotic ionophore A23187 selectively forms an electrically neutral "encounter complex" with positively charged calcium ions. This hydrophobic molecule is capable of moving across a number of different cell membranes, and once the complex enters the cell, the calcium ion is released. This increase in intracellular free calcium has been shown to stimulate the secretion of a variety of substances such as histamine from rodent mast cells and human basophils, amylase and insulin from pancreatic cells, the hormone vasopressin from pituitary cells, the neurotransmitter dopamine from neurons, seratonin from platelets, and catecholamines from adrenal glands. In addition, the A23187 calcium ionophore has been shown to activate sea urchin eggs.

With an ever-increasing world demand for food, there is constant pressure to increase the efficiency of production of food. Ruminant nutritionists have long sought means to manipulate and improve the efficiency of ruminal fermentation. Dietary manipulation was initially used to achieve this goal, but during the last decade a number of active antibiotic compounds, produced by various strains of Streptomyces, were discovered which improve metabolic efficiency. Although originally administered to poultry as anticoccidials, these carboxylic polyether antibiotic compounds, including monensin, lasalosid, salinomycin and narasin, have been found to exhibit ionophoric activity.

Since their discovery, antibiotic ionophores have been used extensively as feed additives to increase the efficiency of the production of poultry and ruminants. Studies have indicated that, when ionophores are added to feed, the growth of pathogens and other microorganisms within the digestive tract is inhibited, thus enhancing the efficient utilization of nutrients in the feed.

The various antibiotic ionophores appear to improve the efficiency of conversion from grain to meat by increasing the efficiency of metabolism in the rumen, improving nitrogen metabolism, and by retarding feedlot disorders such as chronic lactic acidosis and bloat. These effects are caused by a shift in the rumen microflora from bacteria less efficient in fermenting ingested feed to more bacteria that are more efficient. The change in rumen microflora population is brought about by a differential susceptibility of the bacteria to ion flux across their membranes. This influx of ions causes the bacterial cells to swell and burst.

Although antibiotic ionophores have greatly increased the efficiency of production of feed animals, the use of such additives has not been without problems. When antibiotics are mixed in animal feed, the compounds are spread throughout the environment exposing microorganisms to the antibiotics. The constant exposure of the microorganisms to antibiotics causes a resistance to antibiotics which in turn causes infections which are especially severe and difficult to treat.

SUMMARY OF THE INVENTION

In accordance with the present invention, a new class of biologically-active copolymers capable of affecting biological systems in many different ways is provided. The biologically active copolymers of the present invention are capable of stimulating the growth of an organism and stimulating the production of T-cells, peripheral lymphoid tissue, and bone marrow cells of an animal.

The biologically active copolymers of the present invention also have a wide variety of effects on individual cells. These compounds have ionophoric activity, i.e., they cause certain ions to be transported across cell membranes. The compounds can cause non-cytolytic mast cell degranulation with subsequent histamine release. In addition, it has been found that certain members of this class of biologically-active copolymers are capable of specifically killing certain cancer cell lines. The biologically active copolymers are also effective against certain microorganisms.

The biologically active copolymers of the present invention can be administered orally to animals to provide specific effects on certain microorganisms that reside in the gut of the animal. For example, certain biologically-active copolymers can be administered to chickens to kill various species of coccidia that cause coccidiosis. Additionally, biologically active copolymers are administered to humans or animals to reduce the number of microorganisms in the gut. A preferred use is administering the biologically active copolymers of the present invention to poultry to reduce the number of Salmonella and other microorganisms in the poultry gut.

The biologically-active copolymers can also be added to cattle feed to effect a change in the population of microorganisms normally resident in the rumen. Under normal conditions, the microorganisms digest the cellulose eaten by cattle to form the end-product methane. Methane is essentially unusable by the cattle. By administering the biologically-active copolymers of the present invention orally to the cattle, the copolymer differentially affects the rumen microorganisms so that there is a shift in the rumen population of microorganisms. The end result is a population which allows an increase in propionic acid production and a decrease in lactic acid and methane production. Cattle are capable of using propionate in their own metabolism, thereby increasing the efficiency of food conversion.

Methane produced by ruminant animals is a major contributor to the greenhouse effect. Methane and other hydrocarbon combustion by-products are major constituents of the greenhouse gases. The greenhouse effect is theorized to produce major climatological change in the planet's atmosphere due to the warming of the planet. The planet gets warmer because the gases in the atmosphere, such as methane, trap the radiation from the sun and do not allow the heat to reradiate away from the planet. The greenhouse gases form a thermal blanket that inhibits the release of the radiation from the sun that bombards the earth.

Addition of the biologically-active polymers to the feed of ruminants changes the microbial flora of the gut and thus reduces the amount of methane produced by the ruminants. The reduction of methane aids not only in the increased growth of the ruminants, but has the additional effect of reducing the gas that is a major factor in producing the greenhouse effect.

The biologically-active polymers also have a role in inhibiting the adhesion of microorganisms to surfaces. Adhesion of microorganisms to surfaces is the first step in the causation of many medical, dental and public health problems. If microorganisms can be prevented from attaching to a surface, then fewer microorganisms will be capable of either invading that surface or being carried to another site of attachment. If fewer microorganisms are capable of attaching, then these will be less able to perpetuate the associated disease.

Biologic effects of the copolymers of the present invention vary with the structure of the polymer. The ability to modify the structure of these polymers to optimize particular biologic effects provides the potential to design synthetic compounds with a precision and ease not possible in other systems.

The biologically-active copolymer of the present invention also comprises a reverse triblock copolymer of polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 2,000 and 10,000, and "a" represents a number such that the percentage of hydrophile $(C_2H_4O)_a$ is between approximately 2% and 30%.

Another embodiment of the biologically-active copolymer present invention, comprises the reverse triblock copolymer of polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 2,500 and 8,500, and "a" represents a number such that the percentage of hydrophile $(C_2H_4O)_a$ is between approximately 7% and 23%.

Yet another embodiment of the present invention, comprises the reverse triblock copolymer of polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 3,000 and 7,000, and "a" represents a number such that the percentage of hydrophile $(C_2H_4O)_a$ is between approximately 8% and 20%.

A preferred embodiment of the present invention, comprises the reverse triblock copolymer polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 5,000 and 6,000, and "a" represents a number such that the percentage of hydrophile $(C_2H_4O)_a$ is between approximately 14% and 16%.

In general, "a" represents a number such that the percentage of hydrophile $(C_2H_4O)_a$ is between approximately 5% and 30%, with a preferable range of between approximately 7% and 23% and a most preferable range of between 8% and 20%.

The biologically-active copolymer of the present invention is usually administered by a subcutaneous injection, intravenous injection, intramuscular injection, topical administration, transdermal administration, inhalation administration, or transmucosal administration of an effective amount of the copolymer into an animal or human. The biologically-active copolymer of the present invention can be taken orally if it is desired that the copolymer have an effect on alimentary canal microorganisms.

Accordingly, it is an object of the present invention to provide compounds that have a wide variety of biological activities.

Another object of the present invention is to provide compounds that can stimulate the T-cell immune system, including cellular proliferation and modification of cellular function.

Another object of the present invention is to provide a compound that will stimulate the growth of the thymus in an adult animal.

Another object of the present invention is to provide compounds that can stimulate the production of bone marrow cells.

A further object of the present invention is to stimulate bone marrow cellular regeneration and enhance recovery from radiation or other insults toxic to the bone marrow.

Another object of the present invention is to provide compounds that can accelerate and prolong growth.

Another object of the present invention is to provide compounds that have ionophore activity.

Another object of the present invention is to provide compounds that can cause non-cytolytic mast cell degranulation.

Another object of the present invention is to provide compounds that can specifically kill certain tumor cell lines.

Another object of the present invention is to provide compounds that can kill or eliminate microorganisms that reside in the gut.

Another object of the present invention is to specifically immunosuppress an animal against an antigen or a hapten.

Yet another object of the present invention is to provide compounds that are capable of altering the metabolism of ruminant animals so that the efficiency of feed conversion is increased.

Another object of the present invention is to lessen the amount of greenhouse gasses in the atmosphere by reducing the amount of methane released by ruminant animals.

Yet another object of the present invention is to inhibit the adhesion of microorganisms to biological surfaces and to surfaces contacted by biological surfaces in order to reduce the amount of microorganisms that are available for disease production.

Another object of the present invention is to stimulate cell mediated responses.

Another object of the present invention is to stimulate B cell immune responses.

Another object of the present invention is to down regulate autoimmune dysfunction.

These and other objects, features and advantages of the present invention will become apparent after a review of the following detailed description of the disclosed embodiment and the appended claims.

DETAILED DESCRIPTION OF THE PREFERRED EMBODIMENT

The present invention comprises a class of biologically active copolymers which have a wide variety of biological functions which are useful in treating various pathological conditions in both humans and animals and which can also be used to increase the efficiency of food production. The reverse triblock copolymers of the present invention are useful in promoting the growth of animals, stimulating immune function, act as antitumor agents and inhibit growth and adherence of microorganisms.

It is to be noted that when molecular weight is stated in this specification and claims, unless otherwise noted, there is meant the average theoretical hydrophobe molecular weight which equals the total of the grams of the propylene oxide employed per mole of reactive hydrogen compound. The end groups of polyether chains are hydroxyl groups. The number averaged molecular weight can be calculated from the analytically determined "OH Number" expressed in mg KOH/g sample. It should be understood that the absolute value of the molecular weight of a polydisperse compound can be different depending upon the methodology used to determine the molecular weight.

Alternatively, copolymers can be fractionated by a variety of methods, such as gel permeation chromatography, and analyzed for weight percent of oxyethylene and for unsaturation by proton NMR analysis. An example of such an analysis is as follows: Copolymer is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the copolymer. The chromatographic system is equipped with Ultrastyragel $10^3$ A and 500 A in series (Waters, Div. of Millipore, Milford, Mass.). Column size is 7.8 mm internal diameter by 30 cm. Precolumn filters #A-315 with removable 2 $\mu$m fits (Upchurch Scientific, Oak Harbor, Wash.) are used for protection of the columns. 200 $\mu$L (4 mg) of the copolymer in tetrahydrofuran is added to the column and the sample is run with the columns at 40° C. and the detector at 45° C.

All proton NMR analyses are performed in accordance with the NF procedure "Weight Percent Oxyethylene" on a Bruker 300 MHz instrument. The weight percent oxyethylene is calculated from the proton NMR spectra.

It is well recognized in the field of alkylene oxide chemistry that the polyoxyalkylene compositions one obtains by condensing an alkylene oxide with a reactive hydrogen compound are actually mixtures of compounds rather than a single molecular compound. The mixture contains closely related homologues wherein the statistical average number of oxyalkylene groups equals the number of moles of the alkylene oxide employed and the individual members in the mixture contain varying numbers of oxyalkylene groups. Thus, the compositions of this invention are "mixtures" of compounds which are defined by molecular weight of the polyoxypropylene chains and weight percent of oxyethylene groups.

CHEMICAL STRUCTURE

The biologically-active copolymer of the present invention comprises a reverse triblock copolymer of polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 2,000 and 10,000, and "a" represents a number such that the percentage of hydrophile $(C_2H_4O)_a$ is between approximately 2% and 30%.

Another embodiment of the biologically-active copolymer present invention, comprises the reverse triblock copolymer of polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 2,500 and 8,500, and "a" represents a number such that the percentage of hydrophile $(C_2H_4O)_a$ is between approximately 7% and 23%.

Yet another embodiment of the present invention, comprises the reverse triblock copolymer of polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 3,000 and 7,000, and "a" represents a number such that the percentage of hydrophile $(C_2H_4O)_a$ is between approximately 8% and 20%.

A preferred embodiment of the present invention, comprises the reverse triblock copolymer polyoxypropylene/polyoxyethylene having the formula:

$$HO(C_3H_6O)_b(C_2H_4O)_a(C_3H_6O)_bH$$

POP    POE    POP wherein "b" represents a number such that the molecular weight of the hydrophobe $(C_3H_6O)_b$ is between approximately 5,000 and 6,000, and "a" represents a number such that the percentage of hydrophile $(C_2H_4O)_a$ is between approximately 14% and 16%.

In general, "a" represents a number such that the percentage of hydrophile $(C_2H_4O)_a$ is between approximately 5% and 30%, with a preferable range of between approximately 7% and 23% and a most preferable range of between 8% and 20%.

BIOLOGICAL ACTIVITIES

Both agonistic and antagonistic effects of hormones may be elicited by the polymers. Biologic effects of the polymers vary with the structure of the polymer. The ability to modify the structure of these polymers to optimize particular biologic effects provides potential to design synthetic drugs with a precision and ease not possible in other systems.

Many chelating agents, such as ethylenediaminetetraacetic acid (EDTA) consist of oligoamine sites flanked by hydrogen bonding groups. The addition of flanking hydrophobic moieties produce ionophores which are able to transport ions across lipid containing membranes. The compounds of the present invention have this general structure and can act as ionophores in transporting pharmacologically active compounds across artificial membranes. Consequently, the compounds of the present invention represent a new chemical type of ionophore. Some neuropeptide hormones (e.g., substance P) have ionophore activity.

The biologically-active copolymers of the present invention are also effective in causing the cortex of the thymus to begin producing new T-lymphocytes thereby replenishing the immune system with these vital regulatory cells. The copolymers also induce proliferation of large numbers of post-thymic T-cells in the lymph nodes and other peripheral lymphoid tissues.

The biologically active copolymers of the present invention when injected into an animal or a human with an antigen are effective in specifically immunosuppressing the animal or human against that antigen. For purposes of definition, antigens can be broken down into two groups: immunogens and haptens.

Immunogens are compounds which, when introduced into a mammal, will result in the formation of antibodies. Representative of the immunogens are proteins, glycoproteins and nucleoproteins, such as peptide hormones, serum proteins, complement proteins, coagulation factors, and viral or bacterial products. The following is a partial list of representative immunogens.

| proteins | glycoproteins |
| nucleoproteins | peptide hormones |
| serum proteins | complement proteins |
| coagulation factors | microbiocidal products |
| viral products | bacterial products |
| fungal products | specific immunogens |
| albumin | angiotensin |
| bradykinin | calcitonin |
| carcinoembryonic antigen | chloriomamotropin |
| chorionic gonadotropin | corticotropin |
| erythropoietin | Factor VIII |
| fibrinogen | alpha-2-H globulin |
| follitropin | gastrin |
| gastrin sulfate | glucagon |
| gonadotropin | haptoglobin |
| Hepatitis B surface antigen | immunoglobulins |
| insulin | lipotropin |
| melanotropin | oxytocin |
| pancreozymin | placental lactogen |
| prathryin | proangiotensin |
| prolactin | somatotropin |
| somatomadin | somatostatin |
| thyrotropin | vasotocin |
| thymopoietin | vasopressin |
| alpha-1-fetoprotein | myelin |
| myelin basic protein | |

Haptens are compounds which, when bound to an immunogenic carrier and introduced into a chordate, will elicit formation of antibodies specific for the hapten. Haptens, by themselves, are generally poor immunogens, and necessitate immunogenic carriers to elicit an immune response. Representative of the haptens are steroids such as estrogens and cortisones, low molecular weight peptides, other low molecular weight biological compounds, drugs such as antibiotics and chemotherapeutic compounds, industrial pollutants, flavoring agents, food additives, and food contaminants, and/or their metabolites or derivatives.

The biologically active copolymers of the present invention also are active in reducing enteric microorganisms in the gut of humans and animals. Enteric microorganisms and pathogens such as, but not limited to, Salmonella, Escherichia, Klebsiella, Enterobacter, Pseudomonas, Serratia, Shigella, Campylobacter, Proteus, mycobacteria, Pasteurella, Toxoplasma, Edwardsiella, Yersinia, Eimeria and Vibrio are reduced in the gut by treatment with the biologically active copolymers of the present invention.

For example, Salmonella counts in the gut of chickens or other animals are reduced by administering an effective amount of the copolymers of the present invention to the chicken or other animal. A preferred method of administration for treatment to reduce enteric microorganisms in humans and animals includes, but is not limited to, oral ingestion. For example, the copolymers can be administered to animals by admixing the copolymers with standard feed mixtures, which subsequently are fed to animals to be treated.

The biologically active copolymers of the present invention are also active in interfering with the adherence of microbiological organisms to surfaces. Surfaces, as used in this application, refer to both biological surfaces and to non-biological surfaces. Examples of biological surfaces include external surfaces of biological organisms, such as skin or teeth, or internal surfaces such as the mouth, throat, gut, urinary, or genital tract linings. Surfaces can also include tissue or cellular surfaces. Examples of non-biological surfaces include surfaces, whether internal or external, which come into contact with biological materials such as cutting surfaces and packaging equipment surfaces for meat in the meat processing industry or in the home, medical instruments such as dental or surgical tools, or non-biological implements placed the body such as pins, rods or catheters.

Treating the biological or non-biological surfaces, as used in this application, includes any method of exposing the surface to a solution with the block copolymer. Such methods would include bathing, dipping, spraying, wiping, immersing, submerging, plunging, sprinkling, peppering, swabbing, and other applications of the block copolymer to a surface, internal or external, biological or non-biological.

Reducing the number of microorganisms bound to a surface includes decreasing the total number of microorganisms by approximately 25%, more desirably, by approximately 55%. Reducing can be used in terms of reducing the total number of microorganisms bound to a surface and in reducing the ability of microorganisms to bind to surfaces. Reducing is defined as to bring down, as in extent, amount, or degree. Reducing also means to diminish, to grow or cause to grow less or smaller, as in number, amount, or intensity. Other meanings of the term reducing include decrease, lessen, reduce, dwindle, abate, diminish, and subside.

Approximately is used herein to refer to numbers close to the stated value such that the substance to which the number refers to performs substantially the same function to achieve substantially the same result. Alternatively, approximately is generally understood to be in the range of 10% of the stated value.

The block copolymers interfere with the adherence of microbial organisms to surfaces. Though not wishing to be bound by any particular theory, it is thought the block copolymers interfere with adherence by coating the surfaces and altering surface membrane components and coating any microbial organisms that may be present. Interference with the adhesion of the microbiological organism to a surface can prevent the initiation of a disease state if the surface is the cellular surface of a larger organism such as an animal or plant. Interference with the adhesion of the microbiological organism to a surface can also inhibit the transference of the organisms to other surfaces and thus prevent the spread of infection by the microorganism.

The interference by the polymer in the adhesion of microbiological organisms may also be used in products that are used to treat or coat non-biological surfaces, such as tables, floors, meat-processing equipment or implements, which are in contact with biological surfaces contaminated by microbiological organisms, such as dental or surgical tools. The polymer may be incorporated into disinfectants which may have enhanced activity because of the removal of attached microbiological organisms, and not merely from the killing of microbiological organisms.

Surfaces, both biological and non-biological surfaces, can be treated with the block copolymer compositions to prevent microbial attachment. Though not wishing to be bound by any particular theory, it is thought that the block copolymers undergo a change in solubility that is dependent on the pH of the solution. The block copolymers are poorly soluble in aqueous solutions above approximately pH 6. When the pH of the solution is lowered below approximately pH 6, more particularly to pH 5.5 or 5.6, the block copolymers become soluble. An acidic solution, with the block copolymers in solution, could be washed over a surface, either biological or non-biological, with an alkaline surface. The alkaline surface would change the pH of the microenvironment where the solution touches the table, and the block copolymers would become insoluble. The block copolymers would then leave the solution and coat the surface, thus preventing microbial adherence to the surface and coating any microbes that might have been present on the surface. Typical surface treating agents utilize pH dependent mechanisms where acidity is maintained below approximately pH 5.0. The low pH treatment impairs food palatability (taste). Use of the block copolymers of the present invention does not necessitate such harsh treatment and serves to maintain food palatability.

The interference with the adhesion of the microbiological organism may also inhibit the penetration and invasion by the microbiological organism into a biological surface such as a plant or animal. This interference could block the infective process at an early stage and possibly lower the risk of infection.

The adhesion of a microorganism to a surface is an initial step in the colonization of the surface by many microorganisms, such as bacteria, viruses, fungi, and other parasitic organisms. Bacteria includes both gram-positive bacteria and gram-negative bacteria, and other non-gram staining types of bacteria. Usually there is a specific attachment molecule on the microorganism that interacts specifically with a receptor on the surface. This specificity of attachment may limit the attachment of the microorganisms to specific cellular types within a larger organism or may limit the species that the microorganism can colonize. Many bacteria have molecules on their outer surface that specifically attach to cellular receptors present only on specific cellular types. The adhesion to the cellular surface can be mediated by bacterial pili, or by smaller attachment structures such as a fringe or glycocalyx. For example, *Escherichia coli* adheres betters to intestinal lining cells than to oral lining cells, whereas streptococci adhere better to the oral lining cells.

The disease state created by microorganisms is initiated and maintained because the microorganism can adhere to, colonize and subsequently penetrate, the cellular surface of the larger organism. Bacterial adherence to cellular surfaces creates the characteristic disease state associated with that bacteria. For example, adherence of Shigella to intestinal surfaces leads to the disease of shigellosis or bacterial dysentery. One of the major diseases in swine is caused by the filamentous structures on the surface of enteropathic *E. coli.* which binds specifically to porcine intestinal cells. In humans, pathogenicity of *M. pneumoniae* and *N. gonorrhoeae* is dependent on bacterial structures which mediate adherence to tracheal and urethral cells, respectively.

Another area in which bacterial attachment plays a role in pathogenicity is in dental disease. Attachment of bacteria to oral surfaces can lead to such dental diseases as dental caries (cavities) or periodontal disease, destruction of the gums and underlying tissues. Much of the tooth loss found in the human population is due to the destruction of oral tissues by bacteria. Interference with the adherence of the bacteria to these surfaces could inhibit the formation of dental plaque and the attendant problems of caries and periodontal disease.

A major concern of public health officials and the consumer public at large is the contamination of food animals by microbial organisms. In the farming operation, discussed above, the crowded conditions inherent in mass production farming lead to high rates of infection among the animals if an infectious agent is introduced. If the infectious agent can be prevented from adhering to the animal, the spread of infection could be slowed.

If an animal, carrying an microorganism or infectious agent, comes into a slaughter house, the microorganism can be transferred from the initially infected animal to other animals. Even though the animals are dead, the microorganism can still adhere to the animal surfaces and be transmitted to other slaughtered animals at differing stages of processing or even transferred to the consumers who buy the processed meat in stores or restaurants.

During the last decade, the importance of poultry and eggs as vehicles for human salmonellosis has become a major concern of United States regulatory agencies, the poultry/egg consuming public, and the poultry industry. Indeed, control of salmonellosis in commercial poultry has been identified by the Southeastern Poultry and Egg Association and the National Broiler Council as one of the major problems facing the United States poultry industry. The more recent emergency of egg-born *Salmonella enteritidis* (SE) infections in humans has increased industry and regulatory agency interest in this particular strain of Salmonella in egg producing poultry. Furthermore, the emergence of *Salmonella enteritidis* phage type IV in Europe and a number of developing countries continues to cause concern not only because of the zoonotic potential of this isolate, but also due to the animal health problems associated with this more virulent organism.

Due to the molecular structure, surface-active properties, and charge, the polymers of the present invention could interfere with *Salmonella enteritidis* attachment to poultry skin and meat in commercial processing plants where cross-contamination of poultry carcasses with this, and related intestinal pathogens, has become a major problem. An estimated 8–9 billion broiler chickens will be raised and processed in the United States alone in 1994. Currently several expensive procedures are utilized by major poultry companies with the intent of reducing salmonellae and related food-borne pathogens. The presently commercially-available compounds for preventing salmonellae attachment to poultry skin and meat within poultry processing plants all have serious detractors which include low efficacy, high cost, potential human toxicity problems, off-flavors, and environmental pollution problems.

It is to be understood that the preferred biologically-active compound may differ in structure depending upon the biological activity that one desires to elicit.

ADMINISTRATION OF THE BIOLOGICALLY ACTIVE COPOLYMERS

The biologically-active copolymers of the present invention are generally poorly soluble in water. Although the compounds can be injected into an animal or human in aqueous media, it is preferable that the biologically-active copolymers of the present invention be injected as an oil-in-water or water-in-oil emulsion. A mineral oil or other oily substance such as Drakeol 6VR or Drakeol 5 (Penreco, Butler, Pa.) can be used as the oil phase of the emulsion. The aqueous phase can be physiologic phosphate buffered saline or other physiologic salt solution. The ratio of oil to water is preferably between approximately 80:20 and 1:100.

Typically, an oil-in-water emulsion is prepared by mixing between approximately 0.5 to 50 grams of the biologically active copolymers with 5.0 ml of mineral oil in a homogenizer. Next, 95.0 ml of phosphate buffered saline (0.85M sodium chloride, pH 7.3) containing 0.2% polyoxyethylene sorbitan monooleate (Tween 80, Atlas Chemical Industries, Wilmington, Del.) and 50 mg bovine serum albumin (BSA, Sigma Chemical Co., St. Louis, Mo.) is added. The mixture is homogenized thoroughly to form a fine emulsion. The BSA and Tween 80 are used to stabilize the emulsion. It is to be understood that the method of preparing the emulsion, the proportions of oil and water and the type of oil used are not critical. An effective emulsion could be prepared by using a blender, by sonication or other means well known to those of ordinary skill in the art. It is to be further understood that other carriers, emulsifiers, aqueous solutions and adjuvants that are known to those of ordinary skill in the art can be used with the biologically active copolymers of the present invention.

Water-in-oil emulsions are prepared as follows. A stock oil-emulsifier mixture is prepared by blending mineral oil with approximately 5% to 10% of a water-in-oil emulsifier. A mixture of 94.5% oil (Drakeol, Penreco, Butler, Pa.), 4.5% Sorbitan monooleate (Span 80, Atlas Chemical Industries, Wilmington, Del.) and 0.5% polyoxyethylene sorbitan monooleate (Tween 80, Atlas Chemical Industries, Wilmington, Del.) is commonly used. A commercial blend, Freund's incomplete adjuvant (Difco, Detroit, Mich. or Sigma Chemical, St. Louis, Mo.), is also suitable. Approximately 0.5 to 5.0 grams of the biologically active copolymers are added to either 60 ml of the oil-emulsifier mixture or to 40 ml of a physiologic saline solution similar to that used in the oil-in-water emulsion described above. The oil-emulsifier mixture is placed in a blender. The physiologic salt solution is added in three aliquots with vigorous homogenization to insure that a fine water-in-oil emulsion is prepared. Again, it is to be understood that the method of preparing the emulsion is not critical. Numerous variations of the composition of the aqueous and oil phases, their proportions and means of emulsification will be apparent to those skilled in the art and could be used with biologically active copolymers in practicing the invention.

In general, the compositions may be administered by the topical, transdermal, oral, rectal or parenteral (e.g., intravenous, subcutaneous or intramuscular) route. In addition, the compositions may be incorporated into biodegradable polymers allowing for sustained release of the compound, the polymers being implanted in the vicinity of where drug delivery is desired, for example, at the site of a tumor. The biodegradable polymers and their use are described, for example, in detail in Brem et al., *J. Neurosurg.* 74:441–446 (1991). The biologically active copolymers of the present invention are effective with only one injection of compound being administered to an animal. However, in certain cases, subsequent injections may be necessary to achieve maximum stimulation of the immune system or other desired effect. The mode of injection can be subcutaneous, intramuscular or intravenous. A preferred mode of injection is subcutaneous. Intravenous injection is hazardous because of the toxic effects of embolic emulsions.

The optimum amount of the biologically active copolymers in an injection varies with the size of the animal being treated. With animals such as rats or mice, the optimum amount of biologically active copolymers is between approximately 0.01 and 100 mg per animal, with a preferred dose range of between approximately 0.5 to 5 mg per animal. With larger animals a larger quantity of biologically active copolymers is required in the injection for optimum results. With humans, cattle or swine, the dose varies with the age, size and condition of the individual but approximates 5 to 500 mg in most cases.

The poor solubility of the block copolymers can be exploited to provide selective coating of surfaces. Though not wishing to be bound by any particular theory, a change in the solubility of the block copolymers can be effected by changing the pH of the solution containing the block copolymers. The block copolymers are in an emulsion form when the pH of the solution is above approximately pH 6. If acetic acid is added to lower the pH to below approximately pH 6, the block copolymers become soluble. A desirable pH range for solubility of the block copolymer is approximately pH 5.5 to 5.6. If the pH is then raised to above approximately pH 6, the block copolymers become insoluble, leave the solution and coat the surrounding surfaces.

The pH of the surrounding milieu causes the shift in solubility of the block copolymers from an insoluble phase to a soluble phase, or from a soluble phase to an insoluble phase. This phase change leads to the reduction of bacteria retained in the gut of an organism. For example, in humans, substances which are swallowed are subjected to pH conditions in the stomach which are much lower than pH 6. This highly acidic condition is followed by the alkaline conditions of the small intestine which then neutralize the swallowed substances. These physiological conditions would have the following effect on the block copolymers. The block copolymers, in an oil and water emulsion, are ingested. In the stomach, due to the gastric acids, the pH of the solution is reduced to below pH 6 and the block copolymers become soluble. Upon reaching the small intestine, the pH of the solution is raised above pH 6 and the block copolymers become insoluble. Because the block copolymers are no longer soluble, they form a coating on the surfaces of the tissues of the small and large intestines and also coat the bacteria. This coating, formed by the block copolymers leaving the solution, interferes with the attachment of bacteria and thus reduces the number of bacteria that can bind in the intestines.

The change in solubility of the block copolymers due to pH shifts can also be used in the meat processing industry. The block copolymers are dissolved in a solution wherein the pH is kept below approximately pH 6 by a non-toxic acid solution, such as acetic acid. The meat to be processed is then added to the acidic solution with block copolymers.

Localized pH changes, which occur in the microenvironment of the surface of the added meat, increase the local pH to above approximately pH 6 so that the block copolymers are no longer soluble at the surface of the meat. The insoluble copolymers than form a protective coating on the surfaces of the meat and prevent attachment by bacteria. Thus, the meat is protected from bacterial contamination throughout the processing procedures. At the final step before packaging, the meat can be rinsed in an acidic solution to resolubilize the block copolymers and remove the block copolymers from the meat surfaces.

Any of the proposed uses of the block copolymers, to reduce attachment and thus colonization, of microorganisms could take advantage of this solubility shift due to pH changes. The pH of surfaces, including non-biological surfaces, could be selectively lowered and raised to create or remove protective coatings of the block copolymers. Protective coatings could be easily removed by an acidic solution, and a new protective coating could be easily reapplied once the surface's pH was adjusted by a more alkaline wash.

The solubility shift of the block copolymers is theorized to be temperature independent. Thus, surface temperatures would not have to change, just the surface pH would change to effect a change in the solubility of the block copolymers. This temperature independence allows for protective coatings to be applied in processes which must remain cold, such as the processing of meat. Cold conditions also help control the rate of microbial growth.

The reverse triblock copolymers may also be used to promote growth in animals, such as poultry or other food animal. The dosage of the compound will depend on the condition surrounding treatment, the particular compound, and other factors such as weight and condition of the human or animal and the route of administration of the compound. It is to be understood that the present invention has application for both human and veterinary use. For oral administration to humans, a dosage of between approximately 0.01 to 1000 mg/kg/day, preferably between approximately 0.1 and 200 mg/kg/day, and most preferably between approximately 1 to 50 mg/kg/day, is generally sufficient. The recommended dosage for chickens is approximately 10 mg/0.8 kg weight of chicken daily.

The reverse triblock copolymers described above can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of a tumor.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

EXAMPLE

Immune stimulation by the reverse block copolymers

Balb/c mice were immunized using a vaccine preparation of TNP-HEA (trinitrophenyl bonded to hen egg albumin) in a 400 μg/ml to a 20 μg/50 μl dose, with and without a reverse block copolymer, 25R1. Copolymer 25R1 has an approximate total molecular weight of 2700 Daltons, a POE percentage of 10%, thus an approximate POP molecular weight of 2400 Daltons.

Three vaccine preparations were injected into separate groups of 5 BALB/c mice each:

1) ALUM

400 μg of TNP-HEA adsorbed to 5 mg/ml Al(OH)$_3$ to equal 1.7 mg/ml Al.

2) O/W emulsion of TNP-HEA

400 μg/ml TNP-HEA in a microfluidized O/W emulsion containing 2.5% Squalene, 0.25% SPAN 85, 0.25% TWEEN 80, and 0.9% NaCl.

3) O/W-25R1

400 μg/ml TNP-HEA in a microfluidized O/W emulsion containing 5% Squalene, 2.5% 25R1, 0.2% TWEEN 80, and 0.9% NaCl.

The mice were immunized s.c. at the base of the tail on days 0 and 28 with 50 μl vaccine which equals 20 μg of TNP-HEA. The mice were bled on days 0, 14, 28 and 42. The results of the antibody response are reported in Table 1.

TABLE 1

| | SUMMARY OF ANTI-TNP RESULTS Mean UNITS/ML IgG ANTI-TNP: | | | |
|---|---|---|---|---|
| | DAY | | | |
| | 0 (PRIMED) | 14 | 28 BOOSTED | 42 |
| ALUM | 0 | 442 | 1534 | 115,362 |
| O/W | 0 | <55 | 80 | 47,520 |
| O/W + 25R1 | 0 | 62 | 270 | 105,180 |

Conclusions: The adjuvant activity of microfluidized O/W emulsions was compared with that of alum. The basic O/W emulsion had about half the activity of alum. However, addition of the reverse copolymer 25R1 to the microfluidized emulsion gave an adjuvant with activity comparable to alum.

It should be understood, of course, that the foregoing relates only to a preferred embodiment of the present invention and that numerous modifications or alterations may be made therein without departing from the spirit and the scope of the invention as set forth in the appended claims.

What is claimed is:

1. A method for increasing an immune response in a human or animal to an antigen comprising administering to the human or animal the antigen and a nonionic block copolymer having the following formula:

$$HO(C_3H_6O)_b(C_2H_4O)_a(C_3H_6O)_bH$$
$$POP \quad POE \quad POP$$

wherein "b" represents a number such that the molecular weight of the hydrophobe $(C_3H_6O)_b$ is between approximately 2,000 and 10,000, and "a" represents a number such that the percentage of hydrophile $(C_2H_4O)_a$ is between approximately 5% and 30%.

2. The method of claim 1, wherein the block copolymer has the following formula:

$$HO(C_3H_6O)_b(C_2H_4O)_a(C_3H_6O)_bH$$
$$POP \quad POE \quad POP$$

wherein "b" represents a number such that the molecular weight of the hydrophobe $(C_3H_6O)_b$ is between approximately 2,500 and 8,500, and "a" represents a number such that the percentage of hydrophile $(C_2H_4O)_a$ is between approximately 7% and 23%.

3. The method of claim 1 wherein the block copolymer has the formula:

$$HO(C_3H_6O)_b(C_2H_4O)_a(C_3H_6O)_bH$$
$$POP \quad POE \quad POP$$

wherein "b" represents a number such that the molecular weight of the hydrophobe $(C_3H_6O)_b$ is between approximately 3,000 and 7,000, and "a" represents a number such that the percentage of hydrophile $(C_2H_4O)_a$ is between approximately 8% and 20%.

4. The method of claim 1 wherein the block copolymer has the formula:

$$HO(C_3H_6O)_b(C_2H_4O)_a(C_3H_6O)_bH$$
$$POP \quad POE \quad POP$$

wherein "b" represents a number such that the molecular weight of the hydrophobe $(C_3H_6O)_b$ is between approximately 5,000 and 6,000, and "a" represents a number such that the percentage of hydrophile $(C_2H_4O)_a$ is between approximately 14% and 16%.

5. A biologically active composition comprising an antigen and a nonionic block copolymer having the following formula:

$$HO(C_3H_6O)_b(C_2H_4O)_a(C_3H_6O)_bH$$
$$POP \quad POE \quad POP$$

wherein "b" represents a number such that the molecular weight of the hydrophobe $(C_3H_6O)_b$ is between approximately 2,000 and 10,000, and "a" represents a number such that the percentage of hydrophile $(C_2H_4O)_a$ is between approximately 5% and 30%.

6. The composition of claim 5, wherein the block copolymer has the formula:

$$HO(C_3H_6O)_b(C_2H_4O)_a(C_3H_6O)_bH$$
$$POP \quad POE \quad POP$$

wherein "b" represents a number such that the molecular weight of the hydrophobe $(C_3H_6O)_b$ is between approximately 2,500 and 8,500, and "a" represents a number such that the percentage of hydrophile $(C_2H_4O)_a$ is between approximately 7% and 23%.

7. The composition of claim 5, wherein the block copolymer has the formula:

$$HO(C_3H_6O)_b(C_2H_4O)_a(C_3H_6O)_bH$$

POP　　POE　　POP wherein "b" represents a number such that the molecular weight of the hydrophobe $(C_3H_6O)_b$ is between approximately 3,000 and 7,000, and "a" represents a number such that the percentage of hydrophile $(C_2H_4O)_a$ is between approximately 8% and 20%.

8. The composition of claim 5, wherein the block copolymer has the formula:

$$HO(C_3H_6O)_b(C_2H_4O)_a(C_3H_6O)_bH$$

POP　　POE　　POP wherein "b" represents a number such that the molecular weight of the hydrophobe $(C_3H_6O)_b$ is between approximately 5,000 and 6,000, and "a" represents a number such that the percentage of hydrophile $(C_2H_4O)_a$ is between approximately 14% and 16%.

* * * * *

UNITED STATES PATENT AND TRADEMARK OFFICE
CERTIFICATE OF CORRECTION

PATENT NO.    : 5,824,322
DATED         : October 20, 1998
INVENTOR(S)   : Mannarsamy Balasubramanian It is certified that error appears in the above-identified patent and that said Letters Patent is hereby corrected as shown below:

Title page,
Item [57], ABSTRACT, delete the following:
"The reverse copolymers have an inner core of polyoxypropylene (POP) that is flanked on either end by polyoxyethylene (POE)".

and insert in its place:

-- The reverse copolymers have an inner core of polyoxyethylene (POE) that is flanked on either end by polyoxypropylene (POP) --.

Signed and Sealed this

Thirtieth Day of December, 2003

JAMES E. ROGAN
*Director of the United States Patent and Trademark Office*